United States Patent [19]

Ito et al.

[11] Patent Number: 4,841,077
[45] Date of Patent: Jun. 20, 1989

[54] ISOFLAVONE DERIVATIVES, AND SALTS THEREOF, AND CANCEROCIDAL AND IMMUNOSUPPRESSIVE AGENTS CONTAINING THE SAME

[75] Inventors: Noriki Ito, Saitama; Hiroshi Ogawara, Tokyo; Shunichi Watanabe, Saitama, all of Japan

[73] Assignee: Yamanouchi Pharmaceutical Co., Ltd., Tokyo, Japan

[21] Appl. No.: 93,025

[22] PCT Filed: Nov. 17, 1986

[86] PCT No.: PCT/JP86/00586
§ 371 Date: Jul. 16, 1987
§ 102(e) Date: Jul. 16, 1987

[87] PCT Pub. No.: WO87/02982
PCT Pub. Date: May 21, 1987

[30] Foreign Application Priority Data

Nov. 18, 1985 [JP] Japan ............................... 60-259603

[51] Int. Cl.$^4$ ........................................... C07D 311/24
[52] U.S. Cl. ...................................... 549/402; 549/403
[58] Field of Search ....................... 549/402; 514/456

[56] References Cited

U.S. PATENT DOCUMENTS 3,352,754 11/1967 Gazave ............................... 549/402

OTHER PUBLICATIONS

Edwards, J. Natural Products, 42, 85–91 (1979).
Szabo et al., C.A., 83, 178,724r (1975).

Primary Examiner—Nicky Chan
Attorney, Agent, or Firm—Burgess, Ryan & Wayne

[57] ABSTRACT

Novel isoflavone derivatives are provided which have the formula

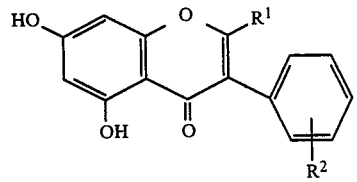

and which exhibit cancerocidal and immunosuppressive activity. The invention also provides pharmaceutical compositions containing the derivatives, methods of use and processes for their preparation.

2 Claims, No Drawings

ISOFLAVONE DERIVATIVES, AND SALTS THEREOF, AND CANCEROCIDAL AND IMMUNOSUPPRESSIVE AGENTS CONTAINING THE SAME

TECHNICAL FIELD

This invention relates to new isoflavone derivatives and salts thereof having cancerocidal and immunosuppressive activity.

BACKGROUND OF THE INVENTION

We formerly found a cancerocidal substance in the product of Pseudomonus sp. YO-0170 strain (FERM-P8170) during a study in search for cancerocidal substances produced by microorganisms, identified it as genistein (chemical name: 5,7,4′-trihydroxyisoflavone,-)—a compound reported in J.A.C.S. (on page 3447, 1951)—, and filed patent application on the manufacturing process of this compound and anticancer agents containing the same (Japanese Patent Publication No. 88235 and No. 89770, 1985).

The above paper reports that genistein has weak estrogenic action, but nothing is known about the cancerocidal and immunosuppressive activity of this compound.

DISCLOSURE OF THE INVENTION

A primary object of this invention is to provide useful compounds having cancerocidal and immunosuppressive activity. A further object of this invention is to provide useful compounds having inhibitory actions against tyrosine-specific protein kinase activity and against the growth of tumor cells, as well as imunosuppressive action. Another object of this invention is to provide drugs of low toxicity having cancerocidal and immunosuppressive activity.

In search for substances showing cancerocidal and immunosuppressive actions, we synthesized various compounds having isoflavone skeleton and found, after screening tests, that the new isoflavone derivatives represented by the general formula (I) and salts thereof exhibit inhibitory action against tyrosine-specific protein kinase activity and immunosupressive action and hence are useful as cancerocidal and immunosupressive agents. This invention was accomplished based on these findings.

Thus this invention relates to new isoflavone derivatives represented by the general formula (I) and salts thereof and to new cancerocidal and immunosuppressive agents containing the same;

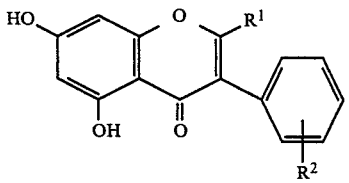

wherein $R^1$ is a radical of

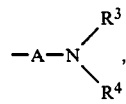

a radical of -CONHR$^5$, a radical of -A-S-R$^6$, or a radical of -COOR$^7$; A denotes a lower alkylene group; $R^3$ and $R^4$ are each a hydrogen atom, a lower alkyl, a cycloalkyl or a sulfur- and nitrogen-containing 5- or 6-membered heterocyclic groups which groups may optionally be substituted by one or two hydroxyl groups, or $R^3$ and $R^4$ may be taken together to form, in conjunction with the adjacent nitrogen, a pyrrolidine, piperidine or morpholine ring; $R^5$ stands for hydrogen atom or a lower alkyl which may be substituted by one or two hydroxyl groups; $R^6$ represents a lower alkyl or a sulfur- and nitrogen containing 5- or 6-membered heterocyclic radical which may optionally be substituted by one or two hydroxyl, carboxyl, or lower alkoxycarbonyl groups; $R^7$ is a lower alkyl which may be substituted by one or two hydroxyl or lower alkoxy groups (a lower alkyl having a carbon number of 1 or 3 through 6, or a lower alkyl substituted by one or two hydroxyl or lower alkoxy groups, when $R^2$ is hydroxyl or a lower alkoxy group); and $R^2$ is hydroxyl, a lower alkoxy or an acyloxy group.

Unless otherwise specified, the term "lower" herein means a linear or branched chain of 1 to 6 carbon atoms. Hence, "lower alkyl radicals" represent linear or branched alkyl groups of 1 to 6 carbon atoms, illustrative examples including methyl, ethyl, propyl, isopropyl, butyl, isobutyl, sec-butyl, tert-butyl, pentyl, isopentyl, neopentyl, tertpentyl, 1-methylbutyl, 2-methylbutyl, 1,2-dimethylpropyl; 1-ethylpropyl, hexyl, isohexyl, 1-methylpentyl, 2-methylpentyl, 3-methylpentyl, 1,1-dimethylbutyl, 1,2-dimethylbutyl, 1,3-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

As examples of "lower alkoxy radicals" there may be mentioned linear and branched alkoxy groups of 1 to 6 carbon atoms, such as methoxy, ethoxy, propoxy, isopropoxy, butoxy, isobutoxy, sec-butoxy, tert-butoxy, pentyloxy, isopentyloxy, hexyloxy and isohexyloxy groups.

Illustrative examples of "lower alkylene radicals" include methylene, ethylene, methylethylene

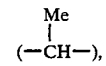

trimethylene, 1-propylene, 2-propylene, tetramethylene, 1-methyltrimethylene, 2-methyltrimethylene, 3-methyltrimethylene, 1-ethylethylene, 2-ethylethylene, pentamethylene, 1-methyltetramethylene, 2-methyltetramethylene, 3-methyltetramethylene, 4-methyltetramethylene and hexamethylene.

"Lower alkyls substituted by one or two hydroxyl groups" mean those lower alkyls as defined above in which any one or two of the hydrogen atoms are substituted by hydroxyl groups (mono- or di-hydroxy lower alkyls). Illustrative examples of "monohydroxy lower alkyls" include hydroxymethyl, 1-hydroxyethyl, 2-hydroxyethyl, 1-hydroxypropyl, 2-hydroxypropyl, 3-hydroxypropyl, 2-hydroxy-1-methylethyl, 1-hydroxybutyl, 2-hydroxybutyl, 3-hydroxybutyl, 4-hydroxybutyl, 3-hydroxy-2-methylpropyl, 3-hydroxy-1-methylpropyl, 2-hydroxy-1,1-dimethylethyl, 1-hydroxypentyl, 2-hydroxypentyl, 3-hydroxypentyl, 4-hydroxypentyl, 5-hydroxypentyl, 4-hydroxy-3-methylbutyl, 6-hydroxyhexyl and 5-hydroxy-4-methylpentyl. Preferred examples of "dihydroxy lower alkyls" include 1,2-dihydroxyethyl, 3,4-dihydroxybutyl, 1-hydroxymethyl-3-hydroxypropyl, 2,2-bis(hydroxymethyl)ethyl, 4,5-dihydroxypentyl and 5,6-dihydroxyhexyl. "Lower alkyls substituted by one or two lower alkoxy groups" mean those lower alkyls as defined above in which any one or two hydrogen atoms are substituted by lower alkoxy groups (mono- or di-lower-alkoxy lower alkyls). Typical examples in which the lower alkoxy is methoxy and the lower alkyl is ethyl include 2-methoxyethyl and 1,2-dimethoxyethyl.

"Lower alkyls substituted by carboxyl or a lower alkoxycarbonyl group" mean those lower alkyls in which any hydrogen atom is substituted by carboxyl or a lower alkoxycarbonyl group (carboxy or lower-alkoxy-carbonyl lower alkyls). Preferred examples of the lower alkoxycarbonyl groups include methoxycarbonyl, ethoxycarbonyl, propoxycarbonyl, isopropoxycarbonyl, butoxycarbonyl, isobutoxycarbonyl, pentyloxycarbonyl and hexyloxycarbonyl. Thus typical examples of carboxy or lower-alkoxy-carbonyl lower alkyls in which the lower alkoxy is methoxy and the lower alkyl is ethyl include carboxyethyl and methoxycarbonylethyl.

Preferred examples of "cycloalkyls" include 5- and 6-membered cyclic alkyls, such as cyclohexyl and cyclopentyl. "Sulfur- and nitrogen-containing, 5- or 6-membered heterocyclic radicals" mean 5- or 6-membered heterocyclic radicals containing sulfur and nitrogen as hetero atoms, in which the hetro ring may be unsaturated, partially saturated or completely saturated. Particularly preferable examples include thiazolyl, isothiazolyl, thiazolinyl, isothiazolinyl, thiazolidinyl, isothiazolidinyl, 2H-1,2-thiazinyl, 2H-1,3-thiazinyl, 4H-1,4-thiazinyl, dihydro-2H-1,2-thiazinyl, dihydro-2H-1,3-thiazinyl, dihydro-4H-1,4-thiazinyl, perhydro-2H-1,2-thiazinyl, perhydro-2H-1,3-thiazinyl and perhydro-1,-thiazinyl radicals.

As preferred "acyloxy radicals" there may be mentioned lower alkanoyloxy radicals, oxaloxy radical and lower alkoxyoxalyloxy radicals. Typical examples of lower alkanoyloxy radicals include acetyl, propionyl, butylyl, isobutylyl, valeryl, isovaleryl, pivaloyl and hexanoyl radicals. The lower alkoxyoxalyloxy radicals are oxalyloxy radical (-O-COCO-) to which a lower alkoxy group is attached. Illustrative examples include methoxalyloxy, ethoxalyloxy, propoxalyloxy, isopropoxalyloxy, butoxalyloxy, pentyloxalyloxy and hexyloxalyloxy radicals.

Some of the compounds represented by the general formula (I) exist in optical, tautomeric and other types of isomeric forms. This invention includes all of these isomers and combinations thereof.

Some of the compounds of this invention are capable of forming salts, and this invention also includes all of these salts. Typical examples include inorganic salts, such as sodium, potassium and ammonium salts; salts with organic bases, such as ethylamine, propylamine, diethylamine, triethylamine, morpholine, piperidine, N-ethylpiperidine, diethanolamine and cyclohexylamine; salts with basic amino acids, such as lysine and ornitine; salts with mineral acids, such as hydrochloric, sulfuric, phosphoric and hydrobromic acids; salts with organic acids, such as acetic, oxalic, citric, maleic, malic, fumaric, tartaric and methanesulfonic acids; and salts with acidic amino acids, such as glutamic and aspartic acids.

The compounds of this invention can be synthesized by various methods. Typical synthetic methods are shown below.

Synthetic method 1

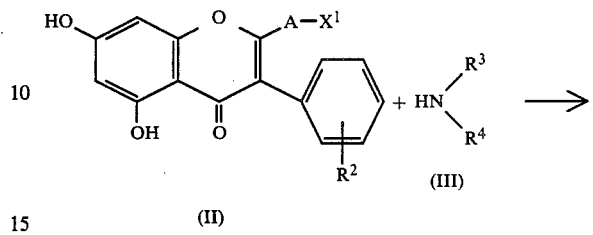

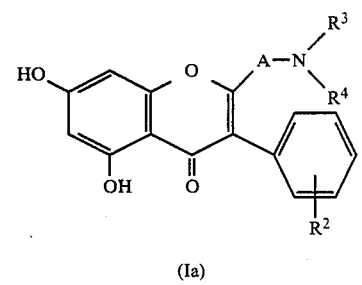

Synthetic method 2

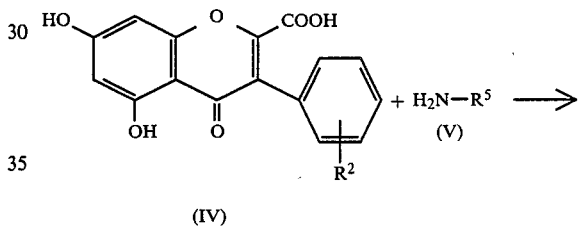

(or, a lower alkyl ester or a reactive derivative thereof)

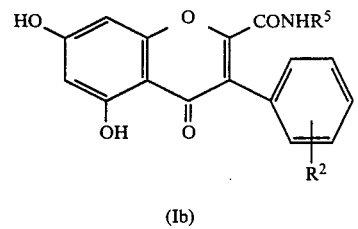

Synthetic method 3

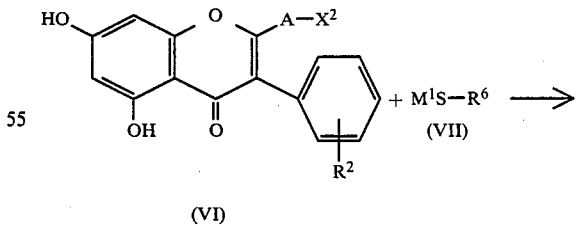

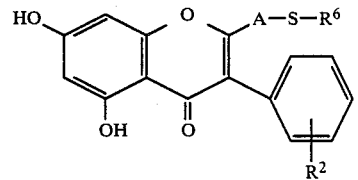

Synthetic method 4

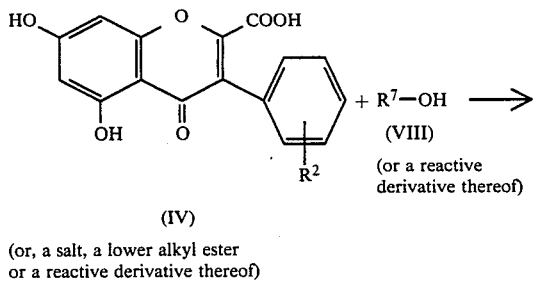

(or, a salt, a lower alkyl ester or a reactive derivative thereof)

Synthetic method 5

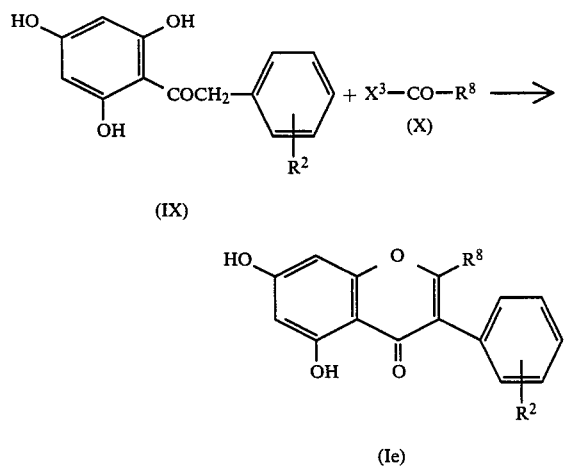

(wherein A, $R^2$, $R^3$, $R^4$, $R^5$, $R^6$, and $R^7$ are as defined above; $X^1$ denotes a halogen atom or an organic sulfonic acid residue; $M^1$ stands for hydrogen atom or an alakli metal atom; $X^2$ represents a halogen atom; $X^3$ expresses a halogen atom or a radical represented by formula $R^8$-CO-O-; $R^8$ is a lower-alkoxycarbonyl, a lower-alkylthio-lower-alkyl, a cycloalkylthio-lower-alkyl or a sulfur- and nitrogen-containing, 5- or 6-membered heterocyclic-thio-lower alkyl which may be substituted by one or two lower alkoxy groups; and $R^{2'}$ is a lower alkoxy or an acyloxy group.)

Halogen atoms include iodine, bromine and chlorine; alkali metals include sodium and potassium; and organic sulfonic acid residues include alkanesulfonic acid residues (e.g., methanesulfonic acid and ethanesulfonic acid residues), and aromatic sulfonic acid residues (e.g., p-toluenesulfonic acid and benzenesulfonic acid residues).

The synthetic methods 1 through 5 mentioned above are described below in more detail.

(Synthetic method 1)

The substituted or unsubstituted amino-lower-alkyl isoflavone derivatives represented by the general formula (Ia) can be prepared by reaction of an amine (III) with a halogeno-lower-alkyl isoflavone derivative or a sulfonyloxylower-alkyl isoflavone derivative (II).

The reaction is carried out preferably in an inert organic solvent, such as benzene, toluene, xylene, dimethylformamide, dichloromethane and chloroform, although it proceeds in the absence of solvent when a halogeno-lower-alkyl isoflavone derivative (II) is used. The amine (III) is preferably used in an amount not smaller than that of compound (II) on molar basis. In some cases, addition of an organic abse (e.g., pyridine, picoline, M,N-dimethylaniline, N-methylmorpholine and trimethylamine) or an inorganic base (e.g., potassium carbonate, sodium carbonate and sodium bicarbonate) is effective in ensuring smooth reaction.

The reaction is generally conducted at room temperature, but may also be carried out at elevated temperatures or under reflux.

The compound (III) may be used for reaction with its amino group blocked with a protective group to avoid side reactions, followed by removal of the protective group after reaction. Examples of the protective group include N-bromosuccinimide, N-bromophthalimide, toluenesulfonyl, acetyl, phenacylsulfonyl, trifluoromethanesulfonyl and bisbenzensulfonyl groups. These protective groups can be easily removed after reaction by usual hydrolysis.

When a sulfonyloxy-lower-alkyl isoflavone derivative (II) is used as starting material, the reaction is preferably carried out at room temperature or under cooling in an inert solvent, such as diethyl ether, tetrahydrofuran, benzene, toluene, xylene, methanol and ethanol, using a compound (III) in an amount not smaller than that of compound (II) on molar basis.

(Synthetic method 2)

The carboxamide compounds represented by the general formula (Ib) can be prepared by reaction of ammonia or an amine (V) with a carboxylic acid (IV), a salt or a reactive derivative thereof.

Examples of reactive derivatives of compound (IV) include acid halides (e.g., acid chloride and acid bromide), acid azides, active esters with N-hydroxybenzotriazole and N-hydroxysuccinimide, symmetric acid anhydrides, mixed anhydrides with an alkyl carbonate, and mixed anhydrides with p-toluenesulfonic acid.

When compound (IV) is used in the form of free carboxylic acid, the reaction is preferably carried out in the presence of a condensation reagent, such as dicyclohexyl carbodiimide and 1,1'-carbonyl-diimidazole.

When carboxylic acid compound (IV) is used in the form of a reactive derivative, the reaction is preferably carried out in an inert solvent, such as pyridine, tetrahydrofuran, dioxane, diethyl ether, benzene, toluene, xylene, dichloromethane, dichloroethane, chloroform, dimethylformamide, ethyl acetate and acetonitrile.

With some of the reactive derivatives, addition of a base, such as triethylamine, pyridine, picoline, lutidine, N,N-dimethylaniline, potassium carbonate and caustic soda, is effective in ensuring smooth reaction. Of these, pyridine serves also as reaction medium.

There is no specific limitation upon the reaction temperature, which should be properly selected depending on the type of reactive derivative used.

When an ester (methyl or ethyl ester) is used as starting material, intended amides (primary or secondary) can be obtained by ammonolysis, which is accelerated by the addition of water or glycol. Liquid ammonia may be employed for this purpose.

The reaction is caried out in the absence of solvent or in an organic solvent, such as methanol, ethanol, benzene, xylene, chloroform, dimethylsulfoxide and tetrahydrofuran.

Ammonium chloride, an alkali metal alcholate (e.g., sodium methoxide), sodium amide or butyl lithium may be added as catalyst. The reaction can thus be carried out at room temperature.

(Synthetic method 3)

The substituted thio-lower-alkyl-isoflavone derivatives represented by the general formula (Ic) can be prepared by reaction of a halogeno-lower-alkyl-isoflavone derivative (VI) with a thiol or an alkali metal salt thereof (VII).

The reaction is carried out in water, an organic solvent or a mixture thereof. Suitable organic solvents include dimethylformamide, dimethylsulfoxide, methanol, ethanol, propanol, acetone, methyl ethyl ketone, tetrahydrofuran, chloroform and dioxane.

When a free thiol is used as compound (VII), the reaction is conducted in the presence of a base, such as potassium carbonate, Triton B, caustic potash, caustic soda and sodium hydride.

There is no specific limitation upon the reaction temperature, but the reaction is generally carried out at room temperature or at elevated temperatures.

(Synthetic method 4)

The compounds represented by the general formula (Id) can be prepared by esterification or ester exchange reaction between a carboxylic acid of formula (IV), a salt, an ester or a reactive derivative thereof with a substituted or unsubstituted alkanol of formula (VIII) or a reactive derivative thereof.

Suitable reactive derivatives of carboxylic acid (IV) include acid halides and acid anhydrides; and halides and sulfonates (e.g., toluenesulfonates and methanesulfonates) are commonly used as reactive derivatives of alkanol (VIII).

When a substituted or unsubstituted alkanol (VIII) is used as alcohol component, it is allowed to react with a free carboxylic acid (IV) in the presence of an acid catalyst (e.g., hydrochloric, sulfuric, trifluoroacetic, ptoluenesulfonic and benzenesulfonic acids) in an organic solvent (e.g., chloroform, carbon tetrachloride, dichloromethane, dichloroethane, benzene, toluene and xylene), or is allowed to react with a reactive derivative of carboxylic acid (IV) (e.g., an acid halide and acid anhydride) in the presence of a base (e.g., trimethylamine, triethylamine, dimethylaniline, pyridine, sodium carbonate and caustic potash) in an organic solvent (e.g., diethyl ether, tetrahydrofuran, ethyl acetate and acetonitrile).

When a substituted or unsubstituted lower alkyl halide or sulfonate of alkanol (VIII) is used as alcohol component, it is allowed to react with a free carboxylic acid (IV) at room temperature or at elevated temperatures in the presence of a base (e.g., caustic soda, caustic potash, potassium carbonate, sodium hydride and triethylamine) in an organic solvent (e.g., methanol, ethanol, acetone, dimethylformamide, ethyl acetate, benzene, toluene and xylene), or is allowed to react with a salt or carboxylic acid (IV) (e.g., sodium and potassium salts) in an organic solvent mentioned above under the same temperature conditions as above.

Ester exchange reaction, on the other hand, may be effected by heating an ester (methyl or ethyl ester) of carboxylic acid (IV) and an unsaturated alkanol (VIII) in the presence of an acid or a base as catalyst. Suitable catalysts include mineral acids (hydrochloric and sulfuric acids), p-toluenesulfonic acid and alkali metal alcoholates.

(Synthetic method 5)

Isoflavone derivatives of this invention may be prepared by cyclization reactions. Of various types of cyclization, reaction of a 2,4,6-trihydroxy-α-phenylacetophenone derivative (IX) with a compound of formula (X) (acid halide or acid anhydride) to form an isoflavone derivative of formula (Ie) is the most preferred because the substituent at position 2 can be simultaneously introduced.

The reaction is carried out in pyridine at room temperature or under cooling by using an acyl halide (X), or by using an acid anhydride (X). When $R^2$ is hydroxyl, $R^{2'}$ in the reaction product will be an acyloxy radical represented by $R^8COO-$.

The compounds of this invention thus prepared can be converted to corresponding salts by usual methods.

The isoflavone derivatives and salts thereof thus formed can be isolated and purified by commonly used techniques, such as concentration, distillation, crystallization, various types of chromatography and recrystallization.

The compounds of this invention and salts thereof show inhibitory action against tyrosine-specific protein kinase activity and against the growth of tumor cells, and are hence useful as cancerocidal agents. What is important is that these compounds are of low toxicity, with no serious side effects as observed in conventional cancerocidal agents. The compounds of this invention also have immunosuppressive activity and are useful as immunosuppressive agents.

Described below are the cancerocidal and immunosuppressive actions of the compounds represented by formula (I).

(1) cancerocidal action (a) Inhibitory action against tyrosine-specific protein kinaso activity The inhibitory action against tyrosine-specific protein kinase activity of the compounds of this invention was measured according to the method described below using tyrosine-specific protein kinase derived from Rous sarcoma virus (src gene $pp60^{src}$).

Method of measurement

Measurement of tyrosine-specific protein kinase activity (src gene $pp60^{src}$ derived from Rous sarcoma virus) (refer to M. S. Colet, R. L. Ericson: Proceeding of the National Academy of Sciences of USA, 75, 2021–2024, 1978)

3Y1 cells (fibroblasts derived from fetal rat kidney) transformed by Rous sarcoma virus (RSV) were cultured, the cultured cells were collected and washed, RIPA buffer solution [containing 0.5% NP40, 0.1% sodium deoxycholate, 50 mM Tris-HCl (pH 7.2), 1 mM phenylmethylsulfonyl fluoride (PMSF) and 0.15M NaCl] was added to the collected cells, the mixture was allowed to stand at 0° C. for 30 minutes to effect solubilization, and the resulting mixture was centrifuged (100,000 × g, 20 minutes). To the supernatant thus collected, was added antiserum obtained from a rabbit cancered by inoculation of RSV, the mixture was incubated at 0° C. for 30 to 60 minutes to cause pp60$^{src}$ to react with antibody, and the immune complex was isolated by mixing with protein A/Sepharose-4B (Pharmacia) and washed with RIPA buffer. The total complex thus obtained (pp60$^{src}$/antibody/protein A/Sepharose-4B) was treated in a solution containing 20 mM Pipes/NaOH (pH 7.2), 5 mM MgCl$_2$, 1 mM DTT and 10 μM [γ-$^{32}$p]ATP (2 mCi/mMol) at 30° C. for five minutes to effect protein kinase reaction, which was terminated by addition a terminating solution containing SDS followed by boiling for three minutes. The reaction mixture was subjected to electrophoresis on 8% SDS/polyacrylamide gel and then to autoradiography, and the radioactivity of cut-out pp60$^{src}$ band was measured on a liquid scintillation counter, thus quantifying the protein kinase reaction and calculating IC$_{50}$ value.

(b) Inhibitory action against the growth of tumor cells

The inhibitory action of the compounds of this invention against the growth of tumor cells was examined by using cells of rats transformed by Rous sarcoma virus (RSV-3Y1 cells).

Test method

RSV-3Y1 cells were cultured in Dulbecco's MEM (Nippon Suisan) containing 10% fetal bovine serum (Gibco) and a compound of this invention at different concentrations (1 μg/ml, 3 μg/ml, 10 μg/ml, 30 μg/ml and 100 μg/ml), and the number of live cells in each dish after 1, 2, 3 and 4 days was measured using trypan blue to determine IC$_{50}$ value.

(2) Immunosuppressive action

Method of measurement

A 5-week-old, male ddy mouse was immunized by abdominal injection with 4×10$^8$ ovine erythrocytes (Mihon Biomaterial Center), and a suspension of a compound of this invention (I) in 0.5% methylcellulose (Shin-Etsu Chemical) solution once a day over a period of four days (two days before immunization and two days after immunization). The spleen was taken out five days after immunization, and the number of antibody-forming cells contained in it was measured as follows according to the method of Cunningham [Cunningham A. J.: Mature, 207, 1106 (1965)]. The splenetic cells were suspended in Eagle's MEM (Nissui Pharmaceutical), ovine erythrocytes and guinea-pig complement were added to this suspension, the resulting mixture was put in a Cunningham chamber (with its both ends sealed with paraffin) and incubated at 37° C. for 90 minutes, and the number of hemolytic plaques (a) (the number of antibody-forming cells) was counted.

Similarly, the number of hemolytic plaques (b) was measured with a mouse not injected with the compound of this invention (control). The antibody-formation inhibition rate was calculated according to the following equation:

$$\text{Inhibition rate} = \frac{b-a}{b} \times 100$$

The compounds of this invention exhibit inhibitory actions against the activity of tyrosine-specific protein kinase derived from oncogene and against the growth of tumor cells, and also show favorable immunosuppressive action.

Since the tyrosine-specific protein kinase is considered to participate in the growth of cancerous cells, the inhibitory action against the activity of this protein kinase exhibited by the compounds of this invention supports their cancerocidal action.

Hence, the compounds of this invention are useful as drugs for the treatment of human and animal cancer. These compounds are also useful as drugs for treatment of autoimmune diseases, such as chronic articular rheumatism, systemic lupus erythematosus, chronic hepatitis and osteoporosis.

The daily dosage of a compound of this invention (I) or a salt thereof is generally 200 to 1000 mg (as active ingredient) for adults, which should be subdivided in 1 to 4 doses. The optimum dose should be determined within the range mentioned above depending on the conditions, age and other factors of the patient.

The compound of this invention may be applied either alone or in combination with other types of chemotherapeutics or with immunotherapeutic agents. As examples of the other types of chemotherapeutics, there may be mentioned cyclophosphamide, vinblastine, vincristine, adriamycin, 6-mercaptopurine, 5-fluorouracil, mitomycin C, bleomycin, aclacinomycin, neocarzinostatin, cytosine arabinoside, actinomycin, and nitrosourea-related drugs. Examples of the immunotherapeutic agents to be used in combination include, among others, clistin, BCG, picibanil, lentinan, interferon and interleukin. Suitable amount of these agents to be used in combination is about 0.1 to 1000% based on the weight of the compound of this invention.

Drugs containing a compound of this invention or a salt thereof as an active ingredient may be administered orally (in the form of tablets, capsules or solutions) or parenterally (in the form of rectal suppositories, injections or pellets). These preparations can be made by usual methods using common carriers and excipients. For tablets, for example, water, glucose, maltose, gum arabic, gelatin, mannitol, starch paste, magnesium trisilicate, talc, cone starch, coloidal silica, potato starch and urea are used as carriers and excipients. Solutions include aqueous or oily suspensions, syrup and elixirs, which can be prepared by commonly used techniques. Suppositories are for rectal administration, which are prepared by using, as base, polyethylene glycol, lanolin, cacao butter, Witeb Sol ® (Dinamit Nobel) and others.

Shown below is an example of capsule formulation.

| | |
|---|---|
| Compound of Example 1 | 200 mg |
| Maltose | 205 mg |
| Crystalline cellulose | 50 mg |
| Hydroxypropylcellulose | 15 mg |
| Starch | 25 mg |
| Magnesium stearate | 5 mg |
| | 500 mg |

To a mixture of the active ingredient, maltose and crystalline cellulose, was added an aqueous solution of hydroxypropylcellulose, the mixture was kneaded and subjected to granulation, the granules thus obtained were dried and mixed with starch and magnesium stearate, and the resulting mixture was filled in No. 1 gelatin capsules.

(Preferred Embodiments of the Invention)

The following Examples will further illustrate the invention.

Of the starting materials used for the synthesis of compounds of this invention, those represented by the general formula (II) are novel compounds, and their manufacturing methods are described in Reference Examples.

Ac, NBS, aq, Et and DMF used in these Examples and Reference Examples mean acetyl group, N-bromosuccinimide, aqueous, ethyl group and dimethylformamide, respectively.

Reference Example 1

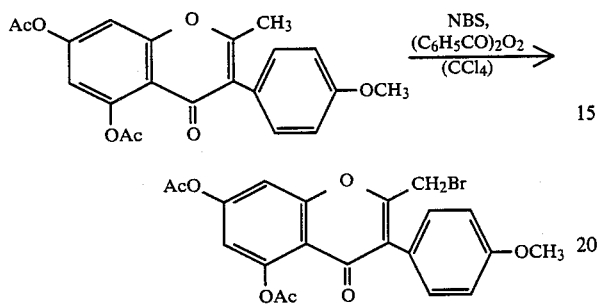

A solution of 5,7-diacetoxy-4'-methoxy-2-methylisoflavone (2 g), benzoyl peroxide (0.1 g) and N-bromosuccinimide (1.4 g) in 120 ml carbon tetrachloride was heated under reflux for 20 hours, the solvent was distilled off under reduced pressure, and the solid residue was treated with water. The crude product collected by filtration was recrystallized from methanol, affording 2.7 g of 5,7-diacetoxy-4'-methoxy-2-bromomethylisoflavone.

Melting point: 181°–183° C.

| Elemental analysis ($C_{21}H_{17}O_7Br$): | | | |
|---|---|---|---|
| | C (%) | H (%) | Br (%) |
| Calcd. | 54.68 | 3.71 | 17.32 |
| Found | 54.52 | 3.68 | 17.15 |

NMR spectrum ($CDCl_3$): δ 2.32 (6H, s) 3.80 (3H, s) 4.16 (2H, s)

Reference Example 2

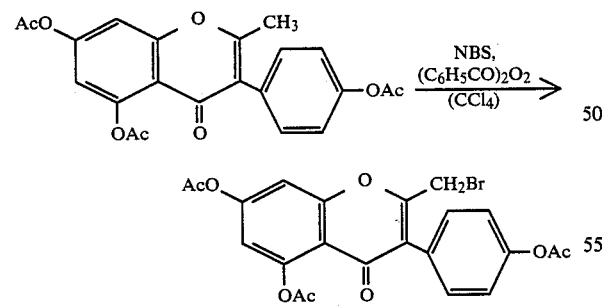

A solution of 4',5,7-triacetoxy-2-methylisoflavone (5 g), benzoyl peroxide (0.3 g) and N-bromosuccinimide (3.9 g) in 300 ml carbon tetrachloride was heated under reflux for 12 hours, the solvent was distilled off under reduced pressure, water was added to the solid residue, the mixture was stirred well, and the crude product collected by filtration was recrystallized from a methanol/chloroform mixed solvent, affording 4.3 g of 4',5,7-triacetoxy-2-bromomethylisoflavone.

Melting point: 214°–216° C.

| Elemental analysis ($C_{22}H_{17}O_8Br$): | | | |
|---|---|---|---|
| | C (%) | H (%) | Br (%) |
| Calcd. | 54.01 | 3.50 | 16.33 |
| Found | 54.20 | 3.28 | 16.15 |

NMR spectrum ($CDCl_3$): δ 2.34 (3H, s), 4.18 (2H, s) 2.36 (3H, s), 6.85 (1H, d) 2.38 (3H, s), 7.30 (1H, d).

Reference Example 3

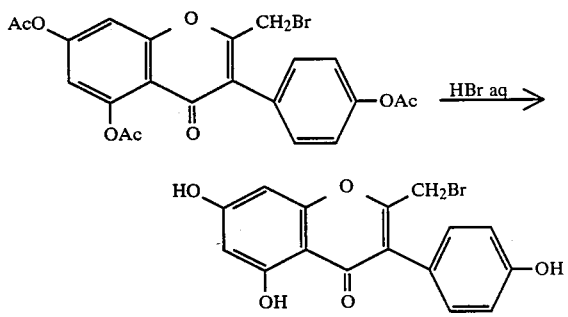

A mixture of 4',5,7-triacetoxy-2-bromomethylisoflavone (1 g) and 48% hydrobromic acid (7 ml) was heated at 100° C. for one hour, the reaction mixture was cooled with stirring, and the solid which separated out was collected by filtration and washed with water, giving 0.7 g of 4',5,7-trihydroxy-2-bromomethylisoflavone.

Melting point: 213°–215° C.

Elemental analysis ($C_{16}H_{11}O_5Br$):

| Elemental analysis ($C_{16}H_{11}O_5Br$): | | | |
|---|---|---|---|
| | C (%) | H (%) | Br (%) |
| Calcd. | 52.92 | 3.05 | 22.00 |
| Found | 52.75 | 2.92 | 21.82 |

NMR spectrum (DMSO-$d_6$): δ 4.34 (2H, s), 6.38 (1H, d), 7.13 (2H, d) 6.20 (1H, d), 6.83 (2H, d)

EXAMPLE 1

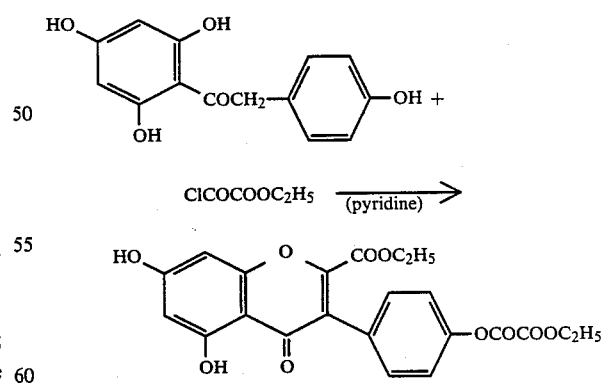

To a solution of 2,4,6-trihydroxy-α-p-hydroxyphenylacetophenone (4.7 g) in 47 ml dry pyridine, was added dropwise 10 ml of ethyloxalyl chloride with stirring under ice cooling so that the temperature will not exceed 5° C., and stirring was further continued at 4° C. for 12 hours. The reaction mixture was poured into ice water, the resulting mixture was extracted with chloroform, and the extract was washed with dilute hydrochloric acid and then water, dried over anhydrous magnesium sulfate and concentrated under reduced pressure. The concentrate was purified by silica gel column chromatography (eluent: chloroform), and the solid crude product thus obtained was recrystallized from ethanol, affording 3.8 g of ethyl 4'-ethoxalyloxy-5,7-dihydroxy-2-isoflavonecarboxylate.

Melting point: 193°–194° C.

| Elemental analysis ($C_{22}H_{18}O_{10}$): | | |
|---|---|---|
| | C (%) | H (%) |
| Calcd. | 59.73 | 4.10 |
| Found | 59.62 | 4.21 |

NMR spectrum (DMSO-$d_6$): δ 0.92 (3H, t), 6.28 (1H, d) 1.14 (3H, t), 6.45 (1H, d) 4.10 (2H, q), 7.32 (4H, s). 4.36 (2H, q)

EXAMPLE 2 filtrate was concentrated under reduced pressure, and the residue was purified by silica gel column chromatography (eluent: chloroform). To the liquid thus obtained was added ethanolic solution of hydrogen chloride, the solvent was distilled off, and the solid which separated out was recrystallized from ethanol, giving 150 mg of 2-(dimethylaminomethyl)-5,7-dihydroxy-4'-methoxyisoflavone hydrochloride.

Melting point: 262°–266° C.

| Elemental analysis ($C_{19}H_{20}NO_5Cl.0.4H_2O$): | | | |
|---|---|---|---|
| | C (%) | H (%) | N (%) |
| Calcd. | 59.27 | 5.45 | 3.64 |
| Found | 59.27 | 5.26 | 3.74 |

NMR spectrum (DMSO-$d_6$): δ 2.72 (6H, s), 6.26 (1H, d), 11.2 (1H, s) 3.80 (3H, s), 6.61 (1H, d), 12.6 (1H, s) 4.26 (2H, s), 7.01 (2H, d), 7.25 (2H, d),

EXAMPLES 3 AND 4

The compounds enumerated below were prepared in the same way as in Example 2.

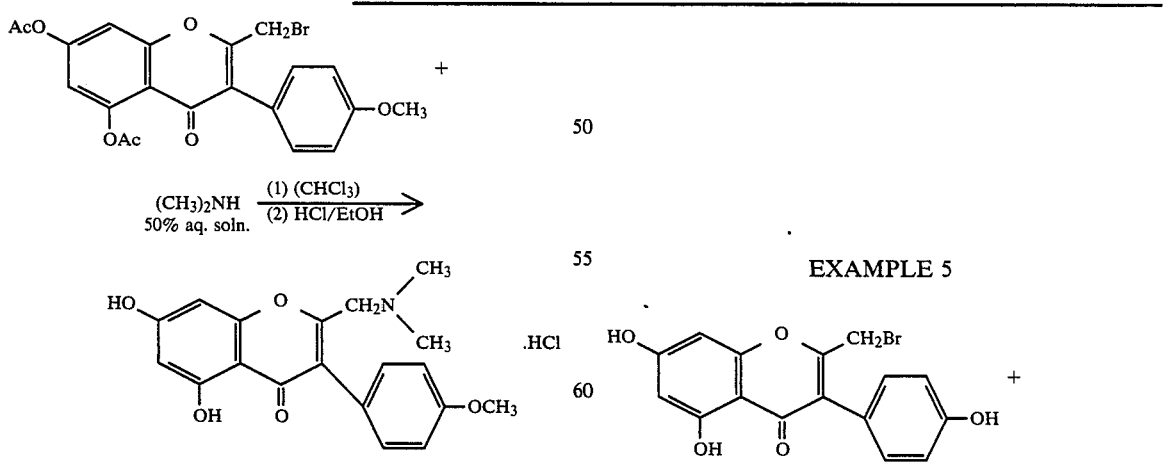

| | Physicochemical Properties |
|---|---|
| Example 3<br>2-(Cyclohexylaminomethyl)-5,7-dihydroxy-4'-methoxy-isoflavone hydrochloride | (1) Melting point: 279–230° C.<br>(2) Elemental analysis ($C_{23}H_{26}NO_5Cl$):<br>　　　C(%)　H(%)　N(%)<br>Calcd.　63.96　6.07　3.24<br>Found　63.91　6.07　3.35<br>(3) NMR spectrum (DMSO—$d_6$)<br>δ: 0.8–2.2 (1H, m)<br>　3.78 (3H, s), 7.02 (2H, d),<br>　4.08 (2H, s), 7.29 (2H, d)<br>　6.25 (1H, d), 6.54 (1H, d), |
| Example 4<br>5,7-Dihydroxy-2-[(2-hydroxy-ethylamino)methyl]-4'-methoxyisoflavone hydrochloride | (1) Melting point: 252–255° C.<br>(2) Elemental analysis ($C_{19}H_{20}NO_6Cl$):<br>　　　C(%)　H(%)　N(%)<br>Calcd.　57.95　5.12　3.56<br>Found　57.82　5.08　3.42<br>(3) NMR spectrum (DMSO—$d_6$)<br>δ: 3.08 (2H, t), 6.24 (1H, d),<br>　3.68 (2H, t), 6.56 (1H, d),<br>　3.82 (3H, s), 7.03 (2H, d),<br>　4.14 (2H, s), 7.29 (2H, d) |

To a solution of 5,7-diacetoxy-4'-methoxy-2-bromomethylisoflavone (500 mg) in 5 ml chloroform, was added 240 mg of 50% aqueous solution of dimethylamine at room temperature with stirring. After one hour, the solid which separated out was filtered off, the

EXAMPLE 5

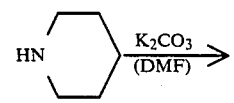

-continued

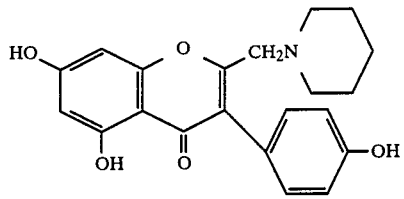

4′,5,7-Trihydroxy-2-bromomethylisoflavone (160 mg) was dissolved in 2 ml, N,N-dimethylformamide, 100 mg piperidine was added to the solution, and the mixture was stirred at room temperature for three hours. The solvent was distilled off under reduced pressure, the residue was purified by silca gel column chromatography (chlorofrom: methanol=96:4), and the solid thus obtained was recrystallized from ethanol, giving 150 mg of 4′,5,7-trihydroxy-2-piperidinomethylisoflavone.

Melting point: 265°–267° C.

| Elemental analysis ($C_{21}H_{21}NO_5$): | | | |
|---|---|---|---|
| | C (%) | H (%) | N (%) |
| Calcd. | 68.65 | 5.76 | 3.81 |
| Found | 68.73 | 5.58 | 3.73 |

NMR spectrum (DMSO-$d_6$) δ 1.36 (6H, m), 6.36 (1H, d) 2.28 (4H, m), 6.77 (2H, d) 3.32 (2H, s), 7.05 (2H, d) 6.18 (1H, d), 12.88 (1H, s)

EXAMPLE 6

The following compound was prepared in much the same manner as in Example 5, except that 2-aminothiazoline was used in place of piperidine.

| Physicochemical Properties | |
|---|---|
| Example 6 | |
| 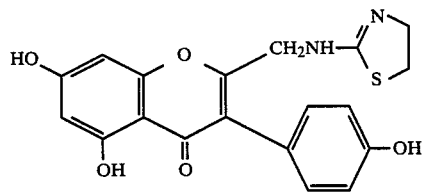 4′,5,7-Trihydroxy-2-[(2-thiazolin-2-ylamino)methyl]isoflavone | (1) Melting point: Gradually decomposes. (no definite dec. point) (2) Elemental analysis ($C_{19}H_{16}N_2O_5S$): <br> C(%) H(%) N(%) S(%) <br> Calcd. 59.37 4.20 7.29 8.34 <br> Found 59.14 4.05 7.11 8.10 <br> (3) NMR spectrum (DMSO—$d_6$) <br> δ: 3.12 (2H, t), 6.32 (1H, d), <br> 3.51 (2H, t), 6.77 (2H, d), <br> 4.38 (2H, s), 7.09 (2H, d) <br> 6.18 (1H, d), |

EXAMPLE 7

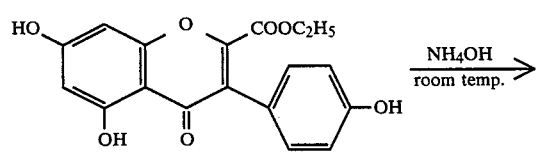

A mixture of ethyl 4′,5,7-trihydroxy-2-isoflavonecarboxylate (120 mg) and 28% ammonia (2 ml) was stirred at room temperature for three hours, water was distilled off under reduced pressure, and the solid residue was recrystallized from methanol, affording 65 mg of 4′,5,7-trihydroxy-2-isoflavonecarboxamide.

Melting point: >300° C.

| Elemental analysis ($C_{16}H_{11}NO_6$): | | | |
|---|---|---|---|
| | C (%) | H (%) | N (%) |
| Calcd. | 61.35 | 3.54 | 4.47 |
| Found | 61.24 | 3.50 | 4.58 |

NMR spectrum (DMSO-$d_6$): δ 6.25 (1H, d), 6.45 (1H, d), 6.77 (2H, d), 7.13 (2H, d), 9.52 (1H, s), 11.0 (1H, s), 12.7 (1H, s)

EXAMPLE 8

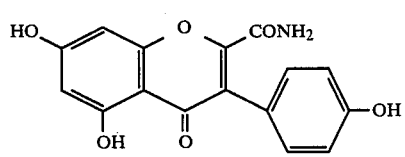

A mixture of ethyl 4′,5,7-trihydroxy-2-isoflavonecarboxylate (100 mg) and 30% methanolic solution of methylamine (5 ml) was stirred at room temperature for 30 minutes, the solvent was distilled off under reduced pressure, and the solid residue was recrystallized from methanol, affording 50 mg of 4′,5,7-trihydroxy-N-methyl-2-isoflavonecarboxamide.

Melting point: 193°–195° C.

| Elemental analysis ($C_{17}H_{13}NO_6$): | | | |
|---|---|---|---|
| | C (%) | H (%) | N (%) |
| Calcd. | 62.39 | 4.04 | 4.28 |
| Found | 62.26 | 4.12 | 4.35 |

NMR spectrum (DMSO-$d_6$): δ 2.32 (3H, s), 5.90 (1H, d), 6.04 (1H, d), 6.73 (2H, d), 7.05 (2H, d)

EXAMPLE 9

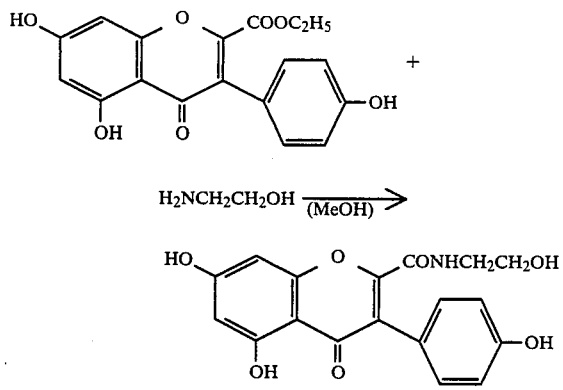

Ethanolamine (100 mg), was added to a solution of 4′,5,7-trihydroxyisoflavonecarboxylate (100 mg) in 2 ml methanol, and the mixture was stirred at room temperature for 12 hours. The solvent was distilled off under reduced pressure, the residue was purified by silica gel column chromatography (chloroform:methanol=95:5), and the solid thus obtained was recrystallized from a methanol/diethyl ether mixed solvent, giving 40 mg of 4′,5,7-trihydroxy-N-(2-hydroxyethyl)-2-isoflavonecarboxamide.

Melting point: 259°–262° C.

| Elemental analysis ($C_{18}H_{15}NO_7$): | | | |
|---|---|---|---|
| | C (%) | H (%) | N (%) |
| Calcd. | 60.51 | 4.23 | 3.92 |
| Found | 60.35 | 4.18 | 3.99 |

NMR spectrum (DMSO-$d_6$): δ 2.8-3.8 (4H, m), 6.24 (1H, d), 6.75 (2H, d), 7.72 (1H, m), 4.68 (1H, m), 6.44 (1H, d), 7.13 (2H, d), 12.7 (1H, s)

EXAMPLE 10

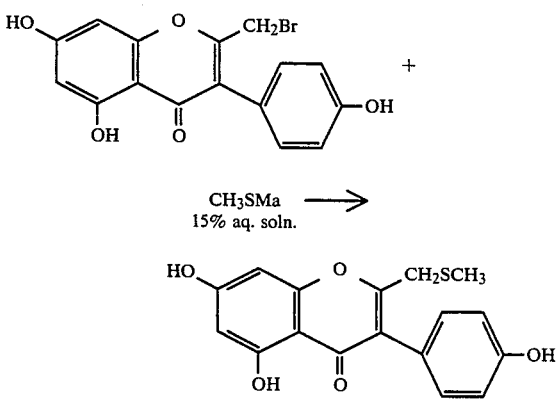

4′,5,7-Trihydroxy-2-bromomethylisoflavone (40 mg) was dissolved in 1 ml N,N-dimethylformamide, 15% aqueous solution of sodium methylmercaptide (90 mg) was added to the solution, and the mixture was stirred at room temperature for 10 hours. The solvents were distilled off under reduced pressure, the residue was purified by silica gel column chromatography (eluent: chloroform), and the solid thus obtained was recrystallized from ethanol, affording 34 mg of 4′,5,7-trihydroxy-2-(methylthiomethyl)isoflavone.

Melting point: 205°–207° C.

| Elemental analysis ($C_{17}H_{14}O_5S$.): | | | |
|---|---|---|---|
| | C (%) | H (%) | S (%) |
| Calcd. | 61.81 | 4.27 | 9.71 |
| Found | 61.95 | 4.39 | 9.63 |

NMR spectrum (DMSO-$d_6$): δ 2.04 (3H, s), 6.20 (1H, d), 5.81 (2H, d), 12.83 (1H, s), 3.52 (2H, s), 6.34 (1H, d), 7.05 (2H, d)

EXAMPLE 11

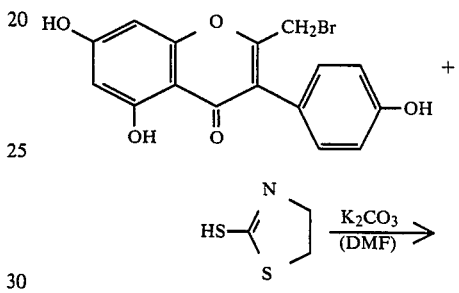

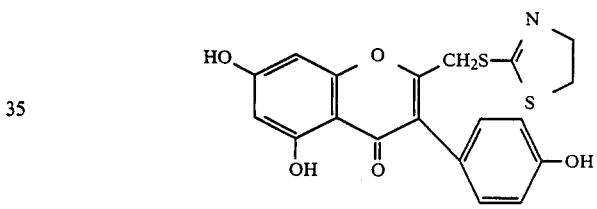

2-Mercaptothiazoline (35 mg) was added to a mixture of 4′,5,7-trihydroxy-2-bromomethylisoflavone (50 mg), anhydrous potassium carbonate (21 mg) and N,N-dimethylformamide (1 ml), and the resulting mixture was stirred at room temperature for 10 hours. The solvent was distilled off under reduced pressure, and the residue was purified by silica gel column chromatography (eluent: chloroform), giving 32 mg of 4′,5,7-trihydroxy-2-[2-thiazolin-2-ylthio)-methyl]isoflavone as amorphous powder.

| Elemental analysis ($C_{19}H_{15}NO_5S_2$): | | | | |
|---|---|---|---|---|
| | C (%) | H (%) | N (%) | S (%) |
| Calcd. | 56.84 | 3.77 | 3.49 | 15.97 |
| Found | 56.58 | 3.61 | 3.25 | 15.72 |

NMR spectrum (DMSO-$d_6$): δ 3.44 (2H, t), 4.06 (2H, t), 4.26 (2H, s), 6.20 (1H, d), 6.32 (1H, d), 6.79 (2H, d), 7.07 (2H, d), 10.9 (1H, s), 12.7 (1H, s),

EXAMPLES 12 AND 13

The following compounds were prepared in much the same manner as in Example 8.

| Physicochemical Properties |
|---|
| Example 12 |

-continued

| | Physicochemical Properties |
|---|---|
| 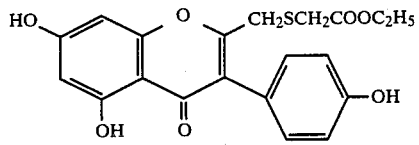<br>Ethyl [[(4',5,7-trihydroxy-2-isoflavonyl)methyl]thio]-acetate | (1) Melting point: 264–265° C.<br>(2) Elemental analysis ($C_{20}H_{18}O_7S$):<br>      C(%)  H(%)  S(%)<br>Calcd.  59.69  4.51  7.97<br>Found  59.81  4.35  7.76<br>(3) NMR spectrum (DMSO—$d_6$)<br>δ: 1.10 (3H, t), 6.18 (1H, d),<br>3.40 (2H, s), 6.34 (1H, d),<br>3.72 (2H, s), 6.81 (2H, d),<br>3.92 (2H, q), 7.09 (2H, d) |
| Example 13 | |
| 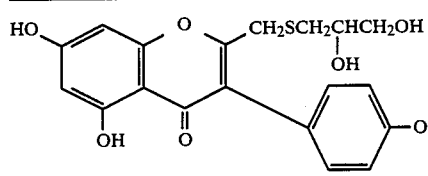<br>2-[[(2,3-Dihydroxypropyl)-thio]methyl]-4',5,7-trihydroxyisoflavone | (1) Melting point: 207–210° C.<br>(2) Elemental analysis ($C_{19}H_{18}O_7S$):<br>      C(%)  H(%)  S(%)<br>Calcd.  58.45  4.65  8.21<br>Found  58.29  4.46  8.12<br>(3) NMR spectrum (DMSO—$d_6$)<br>δ: 3.60 (2H, t), 7.90 (2H, d),<br>6.18 (1H, d), 9.52 (1H, s),<br>6.36 (1H, d), 12.83 (1H, s)<br>6.81 (2H, d), |

EXAMPLE 14

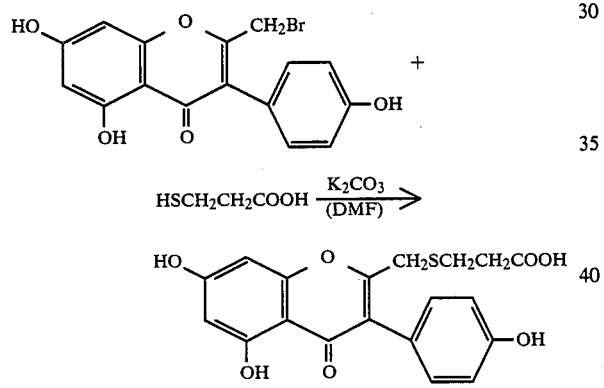

β-Mercaptopropionic acid (60 mg) was added to a mixture of 4',5,7-trihydroxy-2-bromomethylisoflavone (100 mg), anhydrous potassium carbonate (80 mg) and N,N-dimethylformamide (2 ml), and the resulting mixture was stirred at room temperature for 12 hours. The solvent was distilled off under reduced pressure, the residue was dissolved in water, and the solution was acidified by adding 1N-HCl with stirring. The solid which separated out was collected by filtration, washed with water and recrystallized from ethanol, giving 90 mg of 3-[(4',5,7-trihydroxy-2-isoflavonyl)methyl]thio]-propionic acid.

Melting point: 206°–208° C.

| Elemental analysis ($C_{19}H_{16}O_7S$): | | | |
|---|---|---|---|
| | C (%) | H (%) | S (%) |
| Calcd. | 58.76 | 4.15 | 8.26 |
| Found | 58.88 | 4.29 | 8.32 |

NMR spectrum (DMSO-$d_6$): δ 2.36 (2H, t), 6.20 (1H, d), 7.10 (2H, d) 2.72 (2H, t), 6.36 (1H, d), 3.60 (2H, s), 6.81 (2H, d),

EXAMPLE 15

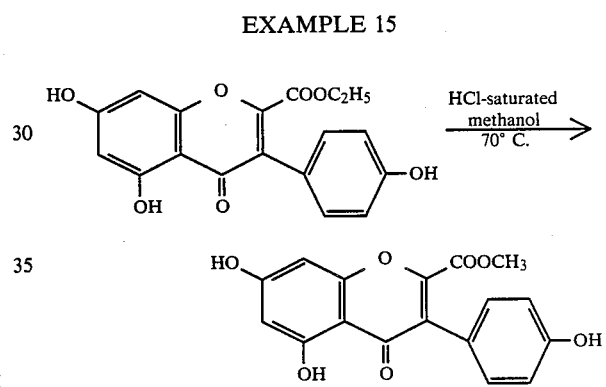

Ethyl 4',5,7-trihydroxy-2-isoflavonecarboxylate (100 mg) was added to 10 ml of methanol saturated with HCl gas, and the mixture was heated at 70° C. with stirring for five hours. The solvent was distilled off under reduced pressure, and the solid residue was recrystallized from methanol, giving 55 mg of 4',5,7-trihydroxy-2-isoflavone-carboxylate.

Melting point: 258°–260° C.

| Elemental analysis ($C_{17}H_{12}O_7$): | | |
|---|---|---|
| | C (%) | H (%) |
| Calcd. | 62.20 | 3.68 |
| Found | 62.31 | 3.59 |

NMR spectrum (CDCl$_3$+DMSO-$d_6$): δ 3.70 (3H, s), 6.37 (2H, d), 10.33 (1H, s), 6.32 (1H, d), 7.09 (2H, d), 12.48 (1H, s), 6.42 (1H, d), 9.04 (1H, s),

EXAMPLE 16

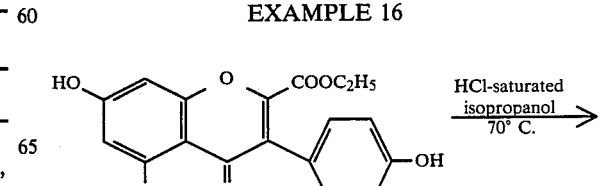

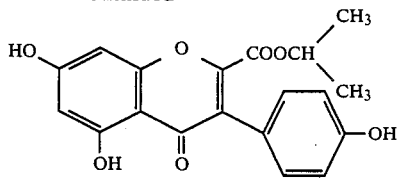

Ethyl 4',5,7-trihydroxy-2-isoflavonecarboxylate (100 mg) was added to 10 ml of isopropanol saturated with HCl gas, and the mixture was heated at 70° C. with stirring for five hours. The solvent was distilled off under reduced pressure, the residue was purified by silica gel column chromatography (eluent: chloroform), and the solid thus obtained was recrystallized from a chloroform/methanol mixed solvent, giving 60 mg of isopropyl 4',5,7-trihydroxy-2-isoflavonecarboxylate.

Melting point: 226°–28° C.

Elemental analysis ($C_{19}H_{16}O_7$):

|  | C (%) | H (%) |
|---|---|---|
| Calcd. | 64.04 | 4.53 |
| Found | 64.21 | 4.46 |

NMR spectrum (DMSO-$d_6$):
δ 1.00 (6H, d), 6.26 (1H, d), 6.70 (2H, d), 4.90 (1H, m), 6.42 (1H, d), 7.07 (2H, d)

EXAMPLE 17

The following compound was prepared in much the same manner as in Example 16, except that HCl-saturated methoxyethanol was used in place of HCl-saturated isopropanol.

Example 17

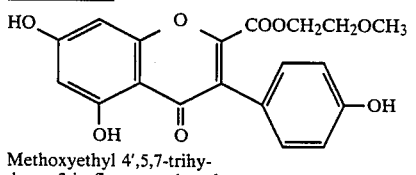

Methoxyethyl 4',5,7-trihydroxy-2-isoflavonecarboxylate

Physicochemical Properties
(1) Melting point: 190–192° C.
(2) Elemental analysis ($C_{19}H_{16}O_8$):

|  | C(%) | H(%) |
|---|---|---|
| Calcd. | 61.29 | 4.33 |
| Found | 61.35 | 4.30 |

(3) NMR spectrum (DMSO—$d_6$)
δ: 3.16 (3H, s), 6.79 (2H, d), 6.26 (1H, d), 7.09 (2H, d), 6.42 (1H, d), 12.5 (1H, s)

EXAMPLE 18

The inhibitory actions of the compounds of Examples 1 through 17 against the tyrosine-specific protein kinase activity and against the growth of RSV-3Y1 cells were measured according to the methods described earlier. The result is summarized in Table 1.

TABLE 1

| Test compd. | IC$_{50}$ (μg/ml) Inhibition against tyrosin-specific protein kinase activity | Inhibition against the growth of RSV-3Y1 |
|---|---|---|
| Example 1 | 1.0 | >100 |
| 2 | >100 | 18.0 |
| 3 | >100 | 16.0 |
| 4 | >100 | >100 |
| 5 | 10.0 | 9.5 |
| 6 | 15.0 | >100 |
| 7 | 10.0 | >100 |
| 8 | 15.0 | >100 |
| 9 | 15.0 | >100 |
| 10 | 5.0 | 20.0 |
| 11 | 5.0 | 20.0 |
| 12 | 4.0 | >100 |
| 13 | 4.0 | >100 |
| 14 | 10.0 | 90.0 |
| 15 | 2.0 | 60.0 |
| 16 | 10.0 | 25.0 |
| 17 | 6.0 | 60.0 |

EXAMPLE 19

The immunosuppressive action of the compounds of Examples 1, 12 and 13 was measured according to the method described earlier. The result is summarized in Table 2.

TABLE 2

| Test compd. | Inhibition Rates of Compounds (I) Dose for each administration (mg/Kg) | antibody-formation inhibition rate (%) |
|---|---|---|
| Example 1 | 1 | 14.4 |
|  | 5 | 28.7 |
|  | 25 | 40.0 |
|  | 50 | 75.8 |
| Example 12 | 5 | 25.3 |
|  | 25 | 50.0 |
| Example 13 | 5 | 27.0 |
|  | 25 | 76.6 |

Note:
Inhibition rate (%) = $\frac{b - a}{b} \times 100$ (Possible Industrial Use)

As may be apparent from the foregoing, the isoflavone derivatives and their salts of this invention are useful as drugs for the treatment of human and animal cancer, and are also useful as drugs for the treatment of human immune diseases, such as chronic articular rheumatism, systemic lupus erythematosus, chronic hepatitis and osteoporosis.

What is claimed is:

1. Isoflavone derivative represented by the general formula (I) or salt thereof;

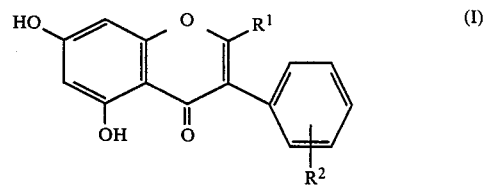

wherein $R^1$ is —COOR$^7$; $R^7$ is a lower alkyl which may be substituted by one or two hydroxyl or lower alkoxy groups and $R^2$ is oxalyloxy or lower alkoxyoxalyloxy.

2. The isoflavone derivative of caim 1 which is ethyl 4'-ethoxalyloxy-5,7-di-hydroxy-2-isoflavonecarboxylate.

* * * * *